United States Patent
Link et al.

(10) Patent No.: US 9,383,354 B2
(45) Date of Patent: Jul. 5, 2016

(54) ANTI-ANTIBODY REAGENT

(71) Applicant: Bio-Rad Laboratories, Inc., Hercules, CA (US)

(72) Inventors: William F. Link, El Cerrito, CA (US); Renato B. del Rosario, Benicia (CA); Randy Sweet, Pinole, CA (US); David L. King, Benicia, CA (US)

(73) Assignee: BIO-RAD LABORATORIES, INC., Hercules, CA (US)

( * ) Notice: Subject to any disclaimer, the term of this patent is extended or adjusted under 35 U.S.C. 154(b) by 0 days.

(21) Appl. No.: 14/598,091

(22) Filed: Jan. 15, 2015

(65) Prior Publication Data

US 2015/0126408 A1 May 7, 2015

Related U.S. Application Data

(63) Continuation of application No. 12/184,775, filed on Aug. 1, 2008, now Pat. No. 8,956,823.

(60) Provisional application No. 60/956,908, filed on Aug. 20, 2007.

(51) Int. Cl.
| | | |
|---|---|---|
| *C12Q 1/04* | (2006.01) | |
| *G01N 33/53* | (2006.01) | |
| *G01N 33/536* | (2006.01) | |
| *G01N 33/543* | (2006.01) | |
| *G01N 33/532* | (2006.01) | |

(52) U.S. Cl.
CPC ........ *G01N 33/54306* (2013.01); *G01N 33/532* (2013.01)

(58) Field of Classification Search
CPC ............ A61K 39/44; A61K 2039/505; A61K 2039/507; C12Q 2545/101; G01N 21/274; G01N 2333/705; G01N 2400/02
See application file for complete search history.

(56) References Cited

U.S. PATENT DOCUMENTS

| | | | |
|---|---|---|---|
| 4,743,542 A | 5/1988 | Graham, Jr. et al. | |
| 5,039,604 A | 8/1991 | Papsidero | |
| 5,126,130 A * | 6/1992 | Lussenhop | ........... C07K 16/088 424/147.1 |
| 5,639,670 A * | 6/1997 | Bergmann | ....... G01N 33/54306 435/7.1 |
| 2003/0108901 A1 | 6/2003 | Kibenge et al. | |

FOREIGN PATENT DOCUMENTS

| | | |
|---|---|---|
| EP | 0289355 A2 | 11/1988 |
| EP | 0603958 A1 | 6/1994 |
| FR | 2652900 A1 | 8/2005 |

OTHER PUBLICATIONS

Stibbs et al., (J. of Clin. Microbio. 1989. vol. 27(11):2582-2588.*
Biagini, R.E. et al.; "Simultaneous measurement of specific serum IgG responses to five select agaents"; 2005, *Anal. Bioanal. Chem.*, vol. 382, pp. 1027-1034.
Stoll, Dieter et al.; "Protein microarrays: Application and future challenges"; 2005, *Current Opinion in Drug Discovery & Development*, vol. 8, No. 2, pp. 239-252.
The International Search Report and Written Opinion from PCT/US2008/073358, dated Jan. 12, 2009 (11 pages).

* cited by examiner

*Primary Examiner* — Ja 'na Hines
(74) *Attorney, Agent, or Firm* — Kilpatrick Townsend & Stockton LLP

(57) ABSTRACT

An anti-antibody reagent for use in a competitive or sandwich simplex or multiplex assay, said reagent comprising one or more labeled anti-antibodies for the primary antibodies to be determined in the assay, the reagent further comprising a corresponding unlabeled anti-antibody in an excess or near excess concentration with respect to their binding partners.

7 Claims, 3 Drawing Sheets

ANTI-ANTIBODY REAGENT

CROSS-REFERENCE TO RELATED PATENT APPLICATIONS

The present application is a continuation of U.S. patent application Ser. No. 12/184,775, filed on Aug. 1, 2008, now U.S. Pat. No. 8,956,823, which claims priority to U.S. Provisional Patent Application No. 60/956,908, Aug. 20, 2007, which are incorporated by reference for all purposes.

BACKGROUND OF THE INVENTION AND PRIOR ART

This invention relates to a novel anti-antibody, or secondary antibody, reagent for use in an immunoassay procedure, to a method for its production and to its use in immunoassays, including both simplex assays (assays for a single analyte) and multiplex assays (assays carried out simultaneously for a plurality of analytes), particularly to automated assays of that type Very generally, the immunoassays are performed to determine whether an analyte, or members of a plurality of analytes, are present in a sample, typically a liquid sample, and also may be used to determine, at least to some degree, the amount of such analytes (if any) in the sample.

Immunoassays of this type are used for numerous purposes, for instance as to determine whether any drugs, proteins, antigens, allergens, pollutants, or other substances are present in a liquid sample, and/or are present in an amount greater or lower than some quantity. The sample could be, for instance, a sample of a human or other mammalian body fluid such as blood, serum, urine, sweat, saliva or stool samples, a liquid sample obtained in a research effort, laboratory procedure or the like, or a sample of water or other liquid material obtained from natural or industrial sources, and the like.

In competitive immunoassays, generally, the sample is placed in contact, or is incubated with, a first antibody (in a simplex assay), or a plurality of first or primary antibodies (in a multiplex assay) for the analytes whose presence and/or amount in the sample is sought to be ascertained, together with molecules of the analyte or analytes to be determined bound or coupled to a solid substrate. An assay is then carried out. The assay typically will be a heterogeneous assay, but could be a homogeneous assay. The solid substrate may have a planar or similar surface, such as a flat plate, a microfluidic device or the walls of wells of a multi-well plate, or it may comprise microparticles or beads. Coupled material is then contacted or incubated with an anti-antibody (in a simplex assay) or a plurality of anti-antibodies (in a multiplex assay) for the primary antibody. The anti-antibodies are tagged or labeled with a detectable label such as a fluorophore, chromophore, radioactive label, etc. that can be detected either visually or, preferably, with an instrument. An appropriate instrument such as a plate reader in the case of a multi-well plate enzyme immunoassay or a flow cytometer when microparticles or beads are used, is employed to detect the label and identify which (if any) analytes are present.

Other immunoassays are used to detect antibodies in serum or plasma that are the result of autoimmune conditions, allergic reactions, or exposure to an infectious agent. In such immunoassays, antigens or a plurality of antigens corresponding to the antibodies of interest are immobilized on a solid surface. The solid substrate may have a planar or similar surface, such as a flat plate, a microfluidic device or the walls of wells of a multi-well plate, or it may comprise microparticles or beads. The specimen is contacted with the surface, and, during an ensuing incubation, antibodies in the specimen, if present, are allowed to bind the immobilized antigens. Coupled material is then contacted or incubated with an anti-antibody (in a simplex assay) or a plurality of anti-antibodies (in a multiplex assay) for the antibody in the specimen. The anti-antibodies are tagged or labeled with a detectable label such as a fluorophore, chromophore, radioactive label, etc. that can be detected either visually or, preferably, with an instrument. An appropriate instrument such as a plate reader in the case of a multi-well plate enzyme immunoassays, or a flow cytometer when microparticles or beads are used, is employed to detect the label and identify which (if any) analytes are present.

Another type of assay can be used to detect a variety of analytes provided that they can be bound simultaneously by two antibodies. This "sandwich" technique consists of incubating the specimen with a first antibody coupled to a solid phase, and a second antibody. If the analyte is present, it is bound by both antibodies, the complexes are separated from the reaction mixture, and the bound second antibody is detected. Typically, the second antibody is labeled with an enzyme, fluorophore, or other species that can be detected directly. Alternatively, a third antibody or other ligand could be used. For example, the second antibodies, or plurality of second antibodies in a multiple assay, could be biotinylated, then detected using streptavidin labeled with an appropriate fluorophore. As another example, the second antibodies could be produced in a different species than was used for the first antibodies (e.g. mouse vs. rabbit) and an appropriately labeled antibody to mouse IgG would detect all bound second antibodies in the mixture.

Assays such as those described above benefit from using labeled anti-antibody reagents that are easily produced, whose optimal working concentration can be easily determined and adjusted, and the use of which results in a robust assay. A robust assay uses reagents in excess or near excess when possible in order to avoid analytical error due to variability in volume of reagent dispensed, time of incubation, dilution by residual wash fluid, and other factors that are rendered less intrusive if concentration of the reagent is not critical. Labeled anti-antibody reagents can be used in excess, but achieving an excess level of anti-antibody activity can lead to generation of excessive amounts of signal.

BRIEF SUMMARY OF THE INVENTION

In one aspect the invention comprises a process for production of an anti-antibody reagent for use in an immunoassay procedure wherein a sample is contacted with a first antibody or a plurality of first antibodies capable of binding to or reacting with analytes whose presence and/or amount in the sample is sought to be determined and with one or more analytes coupled to a solid substrate, and a product of this step is thereafter contacted with one or more labeled anti-antibodies that are capable of coupling with said first antibodies, the process comprising:

including in the one or more labeled antibodies a quantity of one or more of said unlabeled anti-antibodies in an amount such that the total of labeled and unlabeled anti-antibodies is present in an excess or near excess concentration relative to their binding partners, where excess or near excess concentration of the reagent is shown by reducing its concentration by at least 10% and demonstrating that the signal generated by the reagent does not decrease significantly. By "does not decrease significantly" is meant that the measured amount of analyte is affected little, for example, less than about 5%.

In a second aspect the invention comprises a process for conducting a simplex or multiplex immunoassay procedure wherein a sample is contacted with a first antibody or a plurality of first antibodies capable of binding to or reacting with analytes whose presence and/or amount in the sample is sought to be determined, and a product of this step is thereafter contacted with one or more labeled anti-antibodies that are capable of coupling with said first antibodies, wherein the said one or more labeled anti-antibodies further comprises a quantity of one or more unlabeled corresponding anti-antibodies (the same antibody without a label) in an amount such that the total of labeled and unlabeled anti-antibodies is present in an excess or near excess concentration relative to their binding partners, where excess or near excess concentration of the reagent is shown by reducing its concentration by at least 10% and demonstrating that the signal generated by the reagent does not decrease significantly.

In another aspect, the invention comprises a novel anti-antibody reagent for use in a multiplex assay in which a sample is contacted with a first antibody or a plurality of first antibodies each being for a plurality of analytes, said reagent comprising a plurality of labeled anti-antibodies corresponding to the primary antibodies to be determined in the assay, the reagent further comprising a corresponding unlabeled anti-antibody in an excess or near excess concentration with respect to their binding partners.

In still another aspect, the invention comprises a process for production of an anti-antibody reagent for use in an immunoassay procedure wherein a sample is contacted with an antigen or a plurality of antigens capable of binding to or reacting with antibodies whose presence and/or amount in the sample is sought to be determined, and a product of this step is thereafter contacted with one or more labeled anti-antibodies that are capable of coupling with said antibodies from the sample that have bound the said antigens, the process comprising:

including in the one or more labeled anti-antibodies one or more unlabeled corresponding anti-antibodies in an amount such that the total of labeled and unlabeled anti-antibodies is present in an excess or near excess concentration with respect to their binding partners, where excess or near excess concentration of the reagent is shown by reducing its concentration by at least 10% and demonstrating that the signal generated by the reagent does not decrease significantly.

In yet a further aspect the invention comprises a process for conducting a simplex or multiplex immunoassay procedure wherein a sample is contacted with an antigen or a plurality of antigens capable of binding to or reacting with antibodies whose presence and/or amount in the sample is sought to be determined, and a product of this step is thereafter contacted with one or more labeled anti-antibodies that are capable of coupling with said antibodies from the sample, wherein the one or more labeled anti-antibodies further comprises one or more unlabeled corresponding anti-antibodies in an amount such that the total of labeled and unlabeled anti-antibodies is present in an excess or near excess concentration with respect to their binding partners, where excess or near excess concentration of the reagent is shown by reducing its concentration by at least 10% and demonstrating that the signal generated by the reagent does not decrease significantly.

DETAILED DESCRIPTION OF THE INVENTION

Figure 1:
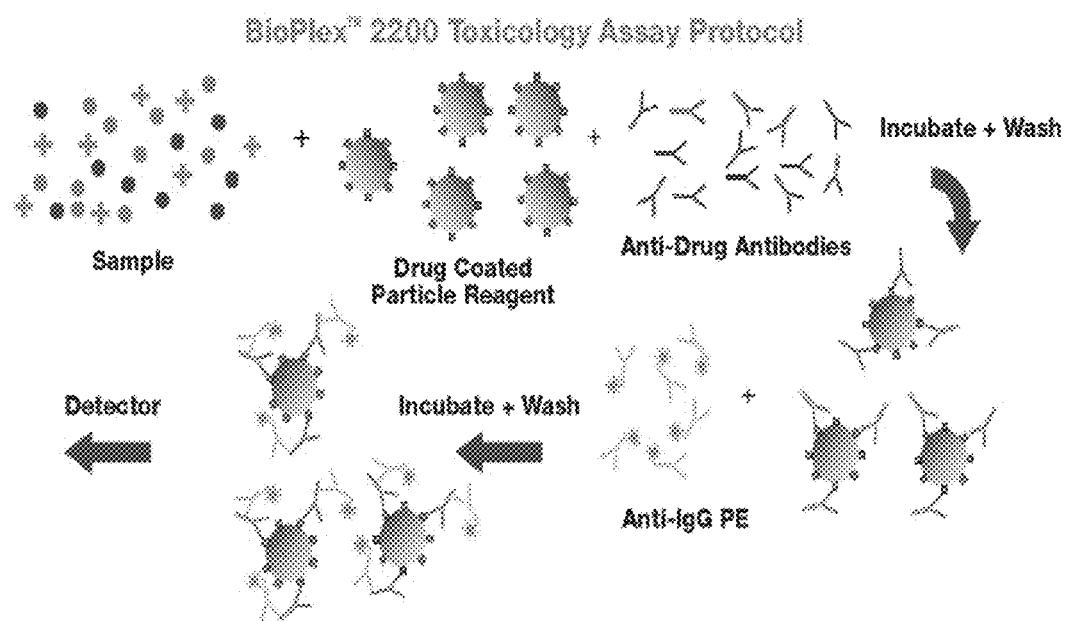
FIG. 1 represents a general depiction of an overall assay as described herein.

The invention herein, which includes a method for preparing an anti-antibody reagent that contains excess unlabeled anti-antibody, the reagent itself and a method of conducting assays using the reagent, provides a way of resolving several problems that can occur in conducting assays, especially multiplex assays carried out on automated equipment.

In such assays, partly due to mechanical aspects of the equipment, the actual incubation time or times for a procedure may vary from a desired value, i.e. the actual incubation time could be shorter or longer than specified by the procedure. This can produce an inaccurate reading, for example the signal can be too large or too small. If the assay is aimed at some quantification of an analyte, for instance to ascertain whether an amount is present above or below a certain value or threshold, the reading may underestimate or overestimate the amount of the analyte present.

In one aspect the invention comprises a process for production of an anti-antibody reagent for use in an immunoassay procedure wherein a sample is contacted with a first antibody or a plurality of first antibodies capable of binding to or reacting with analytes whose presence and/or amount in the sample is sought to be determined and with one or more analytes, which may be drugs, haptens or antigens, coupled to a solid substrate, and a product of this step is thereafter contacted with one or more labeled anti-antibodies that are capable of coupling with said first antibodies, the process comprising:

including in the one or more labeled antibodies a quantity of one or more of said unlabeled anti-antibodies in an amount such that the total of labeled and unlabeled anti-antibodies is present in an excess or near excess concentration relative to their binding partners, where excess or near excess concentration of the reagent is shown by reducing its concentration by at least 10% and demonstrating that the signal generated by the reagent does not decrease significantly. By "does not decrease significantly" is meant that the measured amount of analyte is affected little, for example, less than about 5%.

In a second aspect the invention comprises a process for conducting a simplex or multiplex immunoassay procedure wherein a sample is contacted with a first antibody or a plurality of first antibodies capable of binding to or reacting with analytes whose presence and/or amount in the sample is sought to be determined, and a product of this step is thereafter contacted with one or more labeled anti-antibodies that are capable of coupling with said first antibodies, wherein the said one or more labeled anti-antibodies further comprises a quantity of one or more unlabeled corresponding anti-antibodies (the same antibody without a label) in an amount such that the total of labeled and unlabeled anti-antibodies is present in an excess or near excess concentration relative to their binding partners, where excess or near excess concentration of the reagent is shown by reducing its concentration by at least 10% and demonstrating that the signal generated by the reagent does not decrease significantly.

In another aspect, the invention comprises a novel anti-antibody reagent for use in a multiplex assay in which a sample is contacted with a first antibody or a plurality of first antibodies each being for a plurality of analytes, said reagent comprising a plurality of labeled anti-antibodies for a corresponding to the primary antibodies to be determined in the assay, the reagent further comprising a corresponding unlabeled anti-antibody in an excess or near excess concentration with respect to their binding partners.

In still another aspect, the invention comprises a process for production of an anti-antibody reagent for use in an immunoassay procedure wherein a sample is contacted with an antigen or a plurality of antigens capable of binding to or reacting with antibodies whose presence and/or amount in the sample is sought to be determined, and a product of this step is thereafter contacted with one or more labeled anti-antibodies that are capable of coupling with said antibodies from the sample that have bound the said antigens, the process comprising:

including in the one or more labeled anti-antibodies one or more unlabeled corresponding anti-antibodies in an amount such that the total of labeled and unlabeled anti-antibodies is present in an excess or near excess concentration with respect to their binding partners, where excess or near excess concentration of the reagent is shown by reducing its concentration by at least 10% and demonstrating that the signal generated by the reagent does not decrease significantly.

In yet a further aspect the invention comprises a process for conducting a simplex or multiplex immunoassay procedure wherein a sample is contacted with an antigen or a plurality of antigens capable of binding to or reacting with antibodies whose presence and/or amount in the sample is sought to be determined, and a product of this step is thereafter contacted with one or more labeled anti-antibodies that are capable of coupling with said antibodies from the sample, wherein the one or more labeled anti-antibodies further comprises one or more unlabeled corresponding anti-antibodies in an amount such that the total of labeled and unlabeled anti-antibodies is present in an excess or near excess concentration with respect to their binding partners, where excess or near excess concentration of the reagent is shown by reducing its concentration by at least 10% and demonstrating that the signal generated by the reagent does not decrease significantly.

For purposes of convenience the invention will be described below in the context of its use in an automated multiplex competitive assay for drugs. However, the invention may be used in various types of assays, sandwich as well as competitive, manual as well as automated, simplex as well as multiplex, as described above.

In the assay process, groups of differentiable microparticles or beads coupled to a series of analytes (for example a number of drugs) are incubated with a plurality of first or primary antibodies and the sample, and drugs present in the sample compete for limited antibody binding sites with drugs coupled to the beads. Alternatively the microparticles may be coupled to the antibodies and drug conjugates may be added to a liquid sample for a competitive assay.

The beads are then washed with a buffer containing a detergent and incubated for a period of time with a secondary antibody or anti-antibody reagent containing labeled anti-antibodies, for instance, labeled phycoerythrin-anti-IgG antibodies. In one embodiment a "universal" reporter, consisting of labeled secondary antibodies that will bind all of the drug antibodies bound to the drug derivative on the solid phase, is used. The reporter fluorophore for the immunoassay, phycoerythrin (PE), is preferred in the assays described herein for its high molar extinction coefficient, quantum yield, resistance to photo-bleaching, lack of self-quenching, and stability. However in general, any suitable label may be used to prepare the reagents of this invention.

In accordance with the invention this reagent will contain an excess of unlabeled secondary antibodies, which in the presently described assay preferably is one or more unlabeled anti-IgG antibodies. The system allows for using primary antibodies from more than one species by adding a second antibody. In the present case the system includes anti-mouse antibodies to tag the mouse monoclonals and anti-sheep antibodies to tag sheep polyclonals. Cross-reactivity of the anti-sheep IgG antibody with anti-mouse IgG (and vice versa) is benign. Preferably, interaction of anti-mouse and anti-sheep antibodies is minimized by obtaining both from the same species (for instance, donkey).

The total labeled and unlabeled secondary antibodies are present in the reagent in excess or near excess concentration, where excess or near excess concentration of the reagent is shown by reducing its concentration by at least 10% and demonstrating that the signal generated by the reagent does not decrease. The ratio of unlabeled to labeled anti-antibody is from about 2:1 to about 20:1, depending on the avidity of the antibody, the degree to which the antibody is labeled, and the concentrations required for the given assay. The ratio is determined empirically; in one case the ratio of unlabeled to labeled anti-antibody may be 2:1 to 4:1, and for a different antibody the preferred ratio may be 5:1 to 10:1. The amounts of labeled and unlabeled antibody can be easily adjusted so that the appropriate level of signal is obtained and the total amounts of anti-mouse and anti-sheep antibodies are in excess concentrations. This is as opposed to the customary procedure for preparing a secondary antibody reagent, where the labeling process itself would be optimized to yield the desired level of labeled secondary antibody. The present invention thus allows use of excess amounts of secondary antibody without creating excessive amounts of signal or requiring optimization of labeling methods. Excess amounts of secondary antibody are preferred because they reduce the impact of factors such as pipetting errors, incomplete aspiration after wash steps, and errors in timing of incubation of the assay step that uses the secondary antibody or anti-antibodies. The use of excess amounts of secondary antibody improves assay precision by reducing the effect of pipetting error when the reagent is added to the reaction, and reducing the dilution effect that may occur if wash buffer remains after the wash steps that follow the first incubation. Formulation with excess antibody reaches a saturation level of binding very quickly, allowing a short incubation of 180 seconds that produces a constant level of signal if the incubation is varied by 20 seconds or more. This attribute can improve precision of the assay by greatly reducing the effect of variation in timing of the second incubation, especially in the use of automated assays After a suitable incubation period, the microparticles are assayed, for instance, by flow cytometry for the presence of the drugs in question and/or semi-quantitatively for the amount. A suitable apparatus for such analysis is the BIOPLEX® 2200 analyzer, available from Bio-Rad, Inc. (Hercules, Calif.), which is a fully-automated, random access system utilizing multiplex, magnetic bead and flow cytometric detection technologies.

The panel in this assay uses a set of three reagents—Bead, Primary Antibody and PE—that allow simultaneous immunoassay of the entire panel. The Bead Reagent consists of a suspension of twelve populations of magnetic particles, each population having a unique ratio of classification dyes and a unique, covalently attached drug-protein (or creatinine-protein) conjugate. Another set of particles is coated with a known level of reporter dye and serves as an internal standard. The PE fluorescence of each particle is normalized to the fluorescence of the internal standard to correct for slight fluctuations in detector performance. The Primary Antibody Reagent is a mixture of antibodies specific to each of the drugs in the panel. The PE Reagent contains PE-labeled anti-IgG antibodies.

To perform the assay, 100 µL of Bead Reagent is added to a reaction vessel. Next, 5 µL of specimen are transferred by the analyzer from the specimen tube to a reaction vessel with 45 µL of buffer. Finally, 50 µL of Primary Antibody Reagent are added. Drug in the sample and drug on the particles compete for limited antibody binding sites. The reaction is incubated for 400 seconds, the beads are washed, and 50 µL of PE reagent are added. The PE-labeled secondary antibody binds to primary (anti-drug) antibody bound to the particles. This reaction is incubated for 180 seconds followed by a wash step. The immunoassay is illustrated diagrammatically in FIG. 1.

After the final wash, beads are resuspended and read by the detector which simultaneously measures light at three wavelengths: the two classification dyes and the reporter dye (PE). Thus, for each reaction vessel, particles are identified according to classification dye fluorescence, and emission of PE is quantified for each bead population.

In the first incubation step of the assay, solid phase drug and drug in solution compete for limited antibody binding sites. During this step, timing and antibody concentration are critical because they influence shape of the assay's calibration curve. During the second incubation step, anti-mouse and anti-sheep secondary antibodies bind primary antibody that has been bound to the drug molecules on the solid phase as a result of the first incubation step. Timing of the incubation and antibody concentration during this reaction influence the amount of signal that the assay will generate, but does not alter the shape of the calibration curve. Changes in signal will, however, increase analytical error and increase the imprecision of the assay, particularly if they occur during analysis of specimens.

The second step of the assay where PE Reagent (secondary antibody) is incubated with the reacted beads is prone to three potential sources of error: dilution caused by incomplete aspiration of wash buffer after the wash step at the end of the first incubation, pipetting error caused by inaccurate dispensing of PE Reagent, and incubation error caused by inaccurate timing of the incubation period.

The PE Reagent includes unlabeled anti-mouse and anti-sheep, in order to have an excess amount of both of these secondary antibodies. Since there is an excess amount of secondary antibody, dilution error and pipetting error are greatly reduced or nearly eliminated. This new reagent is very effective, approaching equilibrium within 142 seconds.

EXAMPLES

The following represent examples of the invention. However, they are just that—examples, and not a limitation on the nature of the invention.

Figure 2:
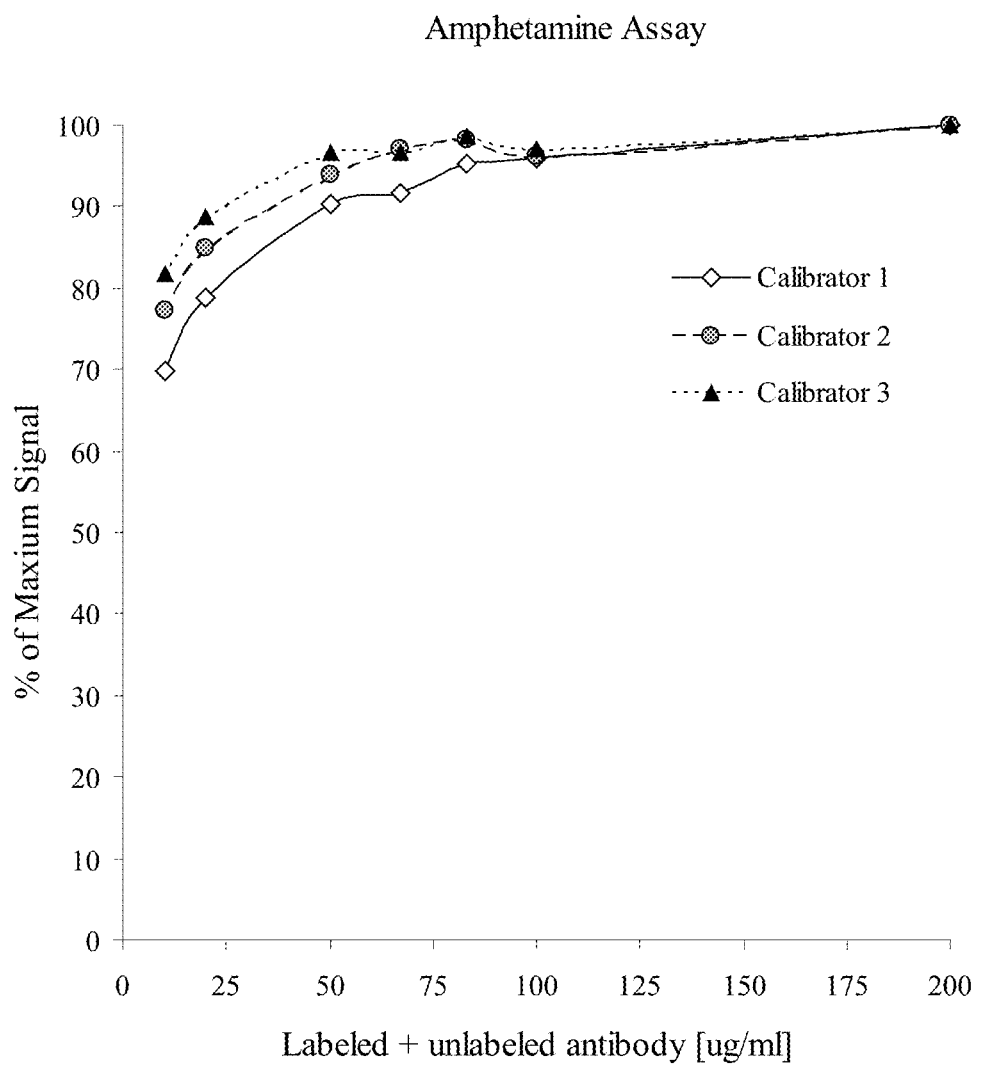
FIG. 2 represents the results of the effect of antibody concentration on signal.

FIG. 2 represents the results of the effect of antibody concentration on signal generated using a mixture of labeled and unlabeled antibody. Unlabeled and labeled anti-antibody were mixed in a ratio of 2.3:1 and used at different concentrations in assays of three different calibrator levels. The example shows that maximum signal is achieved at about 200 µg/mL. Little change in signal is observed if the concentration of the reagent is reduced to 70-100 µg/mL.

Figure 3:
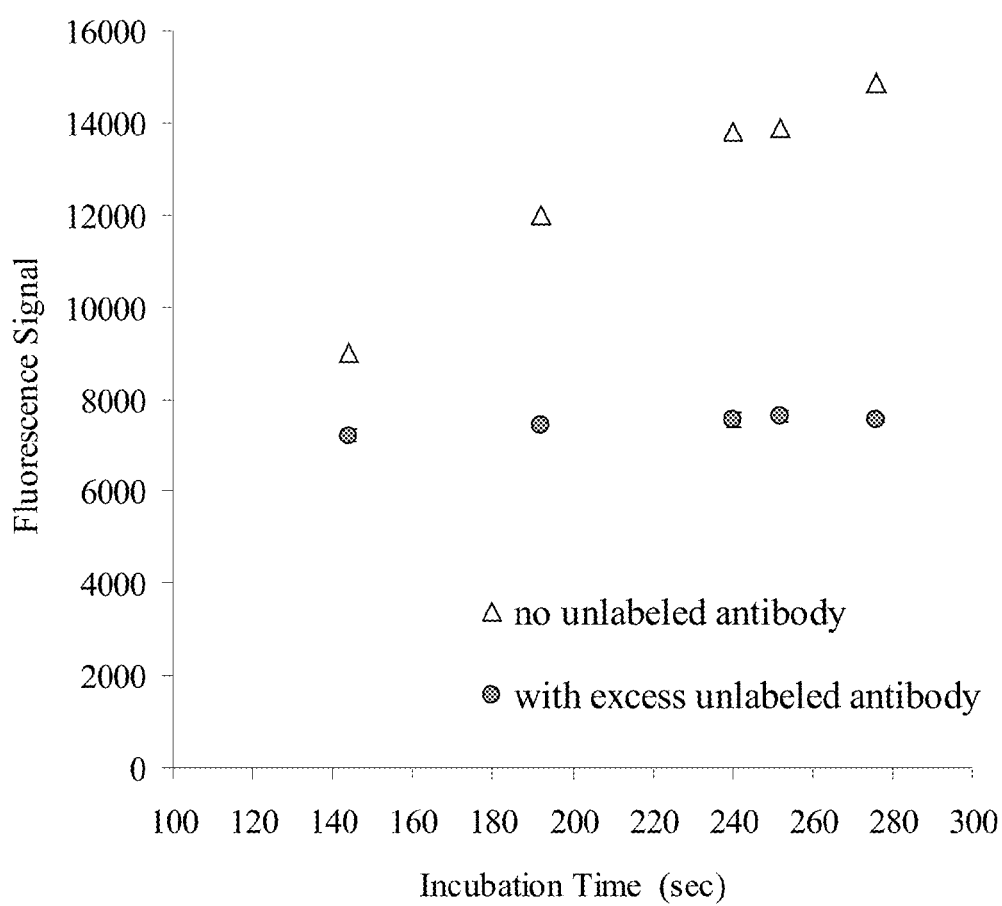
FIG. 3 represents the results of the effect of timing on signal generated with and without excess secondary antibody.

FIG. 3 represents the results of the effect of timing on signal generated with and without excess secondary antibody.

The fluctuation of signal response as a function of the assay $2^{nd}$ incubation period was examined using (a) PE labeled Ab and (b) PE labeled Ab+excess unlabeled Ab. The assay $2^{nd}$ incubation period was incrementally varied from 144-280 sec. FIG. 3 shows a plot of the signal response of the zero calibrator (Cal 1) using Amphetamine as a typical example. In contrast to the PE labeled Ab, the graph shows that the use of labeled Ab+excess unlabeled Ab provided an assay whose signal response was tolerant to incubation timing changes. The same results were obtained for all analytes in the multiplex panel.

The foregoing descriptions are offered primarily for purposes of illustration. Further modifications, variations and substitutions that still fall within the spirit and scope of the invention will be readily apparent to those skilled in the art. All such modifications coming within the scope of the appended claims are intended to be included therein.

All publications, patents, and patent applications cited herein are hereby incorporated by reference in their entirety for all purposes.

What is claimed is:

1. A panel of reagents comprising:
   a binding member that binds an analyte;
   the analyte coupled to a solid support; and
   a mixture comprising (i) an unlabeled antibody that binds the binding member and (ii) a labeled antibody that binds the binding member at an unlabeled:labeled antibody ratio of 2:1 to about 20:1.

2. The panel of claim 1, wherein said mixture contains a ratio of said unlabeled antibodies to said labeled antibodies of from about 2:1 to about 4:1.

3. The panel of claim 1, wherein said mixture contains a ratio of said labeled antibodies to said unlabeled antibodies of from about 5:1 to about 10:1.

4. The panel of claim 1, wherein said binding member is a primary antibody specific for said analyte, and the panel further comprises a secondary antibody with binding affinity to said primary antibody.

5. The panel of claim 1, wherein said binding member is an IgG antibody specific for said analyte, and the panel further comprises an anti-IgG secondary antibody.

6. The panel of claim 1, wherein the analyte is an antigen.

7. The panel of claim 1, wherein the analyte is a hapten.

* * * * *